(12) United States Patent
Turner et al.

(10) Patent No.: US 11,931,526 B2
(45) Date of Patent: Mar. 19, 2024

(54) MEDICAL DEVICE FOR DEPLOYING A CATHETER THAT CAN BE OPERATED WITH A SINGLE HAND, AND A METHOD

(71) Applicant: Wake Forest University Health Sciences, Winston Salem, NC (US)

(72) Inventors: James D. Turner, Winston-Salem, NC (US); Sean Dobson, Winston-Salem, NC (US)

(73) Assignee: Wake Forest University Health Sciences, Winston Salem, NC (US)

( * ) Notice: Subject to any disclaimer, the term of this patent is extended or adjusted under 35 U.S.C. 154(b) by 0 days.

(21) Appl. No.: 18/296,906

(22) Filed: Apr. 6, 2023

(65) Prior Publication Data
US 2023/0256201 A1      Aug. 17, 2023

Related U.S. Application Data

(63) Continuation of application No. 17/048,862, filed as application No. PCT/US2019/028311 on Apr. 19, 2019, now abandoned.

(60) Provisional application No. 62/660,003, filed on Apr. 19, 2018.

(51) Int. Cl.
*A61B 34/20*    (2016.01)
*A61B 8/08*    (2006.01)
*A61M 25/01*    (2006.01)

(52) U.S. Cl.
CPC ....... *A61M 25/0113* (2013.01); *A61B 8/0841* (2013.01); *A61B 34/20* (2016.02); *A61B 2034/2063* (2016.02)

(58) Field of Classification Search
CPC .................. A61B 8/0841; A61B 34/20; A61B 2034/2063
See application file for complete search history.

(56) References Cited

U.S. PATENT DOCUMENTS

| | | | |
|---|---|---|---|
| 4,342,313 A * | 8/1982 | Chittenden | ........ A61M 25/0113 604/523 |
| 10,016,564 B2 * | 7/2018 | Piehl | ................. A61M 5/14244 |
| 2017/0296792 A1 * | 10/2017 | Ornelas Vargas | .. A61M 25/065 |

* cited by examiner

*Primary Examiner* — Serkan Akar
*Assistant Examiner* — Amal Aly Farag
(74) *Attorney, Agent, or Firm* — Thomas | Horstemeyer, LLP

(57) ABSTRACT

A medical device is provided that can be held and operated with a single hand to cause a catheter to be placed at a selected location in a patient's body. The user's other hand is free to perform other tasks, such as operating an ultrasound probe, for example. The medical device may also include a valve that can be operated with the same hand that holds the medical device to open a port to cause a fluid, such as a nerve block agent, for example, to be injected into the patient's body at the selected location.

18 Claims, 3 Drawing Sheets

MEDICAL DEVICE FOR DEPLOYING A CATHETER THAT CAN BE OPERATED WITH A SINGLE HAND, AND A METHOD

CROSS-REFERENCE TO RELATED APPLICATIONS

This application is a continuation of co-pending U.S. non-provisional application entitled "A MEDICAL DEVICE FOR DEPLOYING A CATHETER THAT CAN BE OPERATED WITH A SINGLE HAND, AND A METHOD" having Ser. No. 17/048,862, filed Oct. 19, 2020, which is a U.S. National Phase filing under 35 U.S.C. § 371 of PCT International Application No. PCT/US2019/028311 filed on Apr. 19, 2019, that claims the benefit of and priority to the filing date of U.S. provisional application entitled "A MEDICAL DEVICE FOR DEPLOYING A CATHETER THAT CAN BE OPERATED WITH A SINGLE HAND, AND A METHOD" having Ser. No. 62/660,003, filed Apr. 19, 2018, the contents of which are incorporated by reference herein in their entireties.

TECHNICAL FIELD

The present disclosure generally relates to medical devices, and more particularly, to a medical device for deploying a catheter that can be operated with a single hand of the user to allow the user's other hand to be used to perform other tasks, e.g., operating an ultrasound probe.

BACKGROUND

One of the difficulties associated with current peripheral nerve catheter placement for regional anesthesia (typically for patients having orthopedic procedures, although used in other clinical situations as well) is that it often requires two providers to perform the procedure because the nerve catheter itself is wire reinforced. This causes it to be coiled and at times difficult to manage, and it is virtually impossible for a single provider to thread the catheter while operating an ultrasound probe. Furthermore, it is often desirable to expand the space around nerves with dextrose, saline, or local anesthetic prior to placing the local anesthetic nerve block catheter. This creates the need, at this moment, to either thread the catheter without being able to visualize it under ultrasound or to have a third hand hold the ultrasound probe while the catheter is being threaded. If the catheter is not threaded in the appropriate place, an entirely new kit and/or catheter might be required in order for a new nerve block catheter to be placed.

Some attempts have been made to address this problem by creating a catheter that sits over top of a peripheral nerve block needle and when in proper position, the catheter is threaded over top of the needle. However, many providers do not prefer this technique for various reasons.

Accordingly, a need exists for a medical device for deploying a catheter that can be operated with a single hand.

Furthermore, there remains a need for a medical device that can allow for aspiration and injection with the catheter in position to be deployed; all while freeing up the user's other hand to perform other tasks, such as operating an ultrasound probe, for example.

SUMMARY

In various aspects, medical devices are provided that overcome one or more of the aforementioned problems. For example, medical devices for deploying a catheter are provided that can be operated with a single hand. In various aspects, the medical devices described herein can allow for aspiration and injection with a single hand and with the catheter in position to be deployed. Methods of using the devices are also provided.

In various aspects, a medical device is provided including a housing, the housing having a catheter holder that is configured to hold a catheter in a coiled configuration, the housing having a first opening formed in a forward end thereof through which a distal end of the catheter passes when the catheter is being deployed; a first actuator mechanism mechanically coupled to the housing and to the catheter, the first actuator mechanism being controllable with a digit of a hand of the user to cause the catheter to be fed out of the catheter holder and to move along a catheter pathway of the housing in a first direction; a first port mechanically coupled to, or integrally formed in, the housing, the first port being adapted to introduce a fluid into the housing; and a first valve mechanically coupled to the housing, the first valve being configured to be placed in at least a first position that allows fluid received in the first port to enter a first inner region of the housing and a second position that prevents fluid received in the first port from entering the first inner region of the housing, the first valve being controllable with a digit of a hand of the user to cause the first valve to be placed in one of the first position and the second position.

In various aspects, a medical device is provided that is controllable with a first hand of a user in which the medical device is held to deploy a catheter in a patient's body while operating an ultrasound probe with a second hand of the user. The medical device can include a housing, the housing having a disk-mounting surface and a spindle fixedly secured to the disk-mounting surface and extending away from the disk-mounting surface in a direction substantially normal to the disk-mounting surface, the disk-mounting surface being adapted for mounting a disk thereon such that the spindle mates with an opening formed in the disk to rotationally couple the disk to the housing, wherein the disk holds a coiled configuration of the catheter, the housing having a first opening formed in a forward end thereof through which a distal end of the catheter passes when the catheter is being deployed, the housing having a catheter pathway along which the catheter moves that extends between the first opening and the catheter holder; a first actuator mechanism mechanically coupled to the housing and to the catheter, the first actuator mechanism comprising a plurality of gear wheels, a portion of at least a first gear wheel of the plurality of gear wheels being accessible by the user to allow the user to use a digit of the first hand to rotate the first gear wheel in at least a first direction, wherein rotation of the first gear wheel in the first direction causes the catheter to be fed out of the disk and to move along the catheter pathway in a second direction as the user operates the ultrasound probe with the second hand; a first port mechanically coupled to, or integrally formed in, the housing, the first port being adapted to introduce a fluid into the housing; and a first valve mechanically coupled to the housing, the first valve being configured to be placed in at least a first position that allows fluid received in the first port to enter a first inner region of the housing and a second position that prevents fluid received in the first port from entering the first inner region of the housing, the first valve being controllable with a digit of the first hand to cause the first valve to be placed in one of the first position and the second position as the user operates the ultrasound probe with the second hand.

In various aspects, methods of using the devices described herein are also provided. The methods can be used to deploy a catheter in a patient's body. The methods can include, with a digit of a hand of the user, controlling a first actuator mechanism that is mechanically coupled to a housing of the medical device and to the catheter to cause the catheter to be fed out of a coiled configuration of the catheter held within a catheter holder and to move along a catheter pathway in a first direction, the housing having a first opening formed in a forward end thereof through which a distal end of the catheter passes when the catheter is being deployed; and with a digit of a hand of the user, operating a first valve that is mechanically coupled to the housing to place the first valve in one of a first position and a second position, wherein when the first valve is in the first position, the first valve allows fluid received in a first port of the medical device to enter a first inner region of the housing, wherein when the first valve is the second position, the first valve prevents fluid received in the first port from entering the first inner region of the housing.

Other systems, methods, features, and advantages of medical devices and methods will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various aspects, described below, when taken in conjunction with the accompanying drawings.

DETAILED DESCRIPTION

Figure 1:
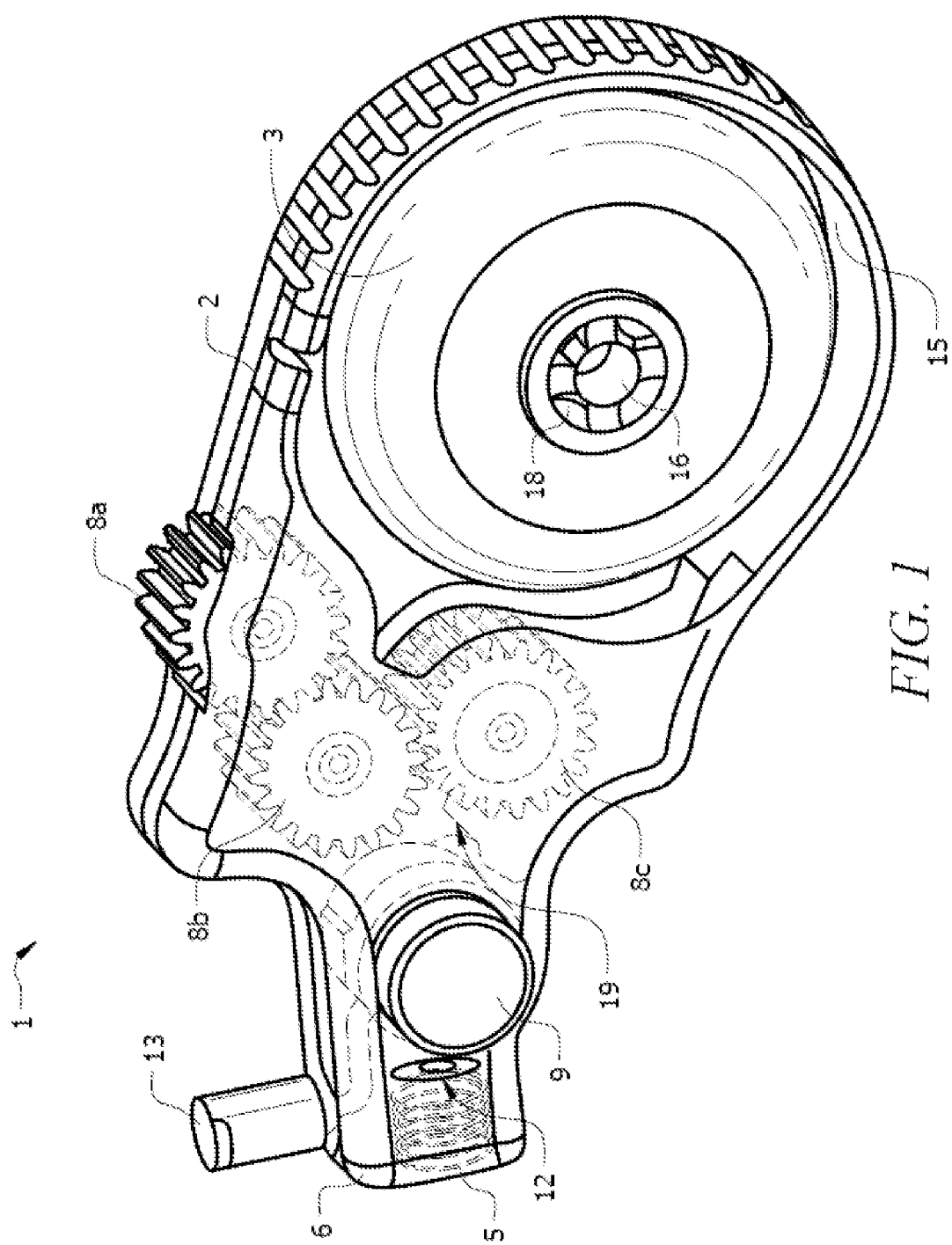
FIG. 1 is a side and rear transparency perspective view of a first exemplary medical device in accordance with the disclosure.

In accordance with the inventive principles and concepts described herein, a medical device is provided that can be held and operated with a single hand to cause a catheter to be placed at a selected location in a patient's body. The user's other hand is free to perform other tasks, such as operating an ultrasound probe, for example. In accordance with an aspect, the medical device also includes a valve that can be operated with the same hand that holds the medical device to open a port to cause a fluid, such as a nerve block agent, for example, to be injected into the patient's body at the selected location.

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Aspects and features of the present disclosure will employ, unless otherwise indicated, medical and surgical techniques, as well as techniques for the design and manufacture of medical devices and surgical tools and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some aspects, the term "about" can include traditional rounding according to significant figures of the numerical value. In addition, the phrase "about 'x' to 'y'", where 'x' and 'y' are numerical values, includes "about 'x' to about 'y'".

In some instances, units may be used herein that are non-metric or non-SI units. Such units may be, for instance, in U.S. Customary Measures, e.g., as set forth by the National Institute of Standards and Technology, Department of Commerce, United States of America in publications such as NIST HB 44, NIST HB 133, NIST SP 811, NIST SP 1038, NBS Miscellaneous Publication 214, and the like. The units in U.S. Customary Measures are understood to include equivalent dimensions in metric and other units (e.g., a dimension disclosed as "1 inch" is intended to mean an equivalent dimension of "2.5 cm"; a unit disclosed as "1 pcf" is intended to mean an equivalent dimension of 0.157 kN/m$^3$; or a unit disclosed 100° F. is intended to mean an equivalent dimension of 37.8° C.; and the like) as understood by a person of ordinary skill in the art.

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in aspects of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

In various aspects, the medical device includes a housing, a first actuator mechanism, a first port and a first valve. The housing can have a catheter holder that is configured to hold a catheter in a coiled configuration. A first opening is formed in a forward end of the housing through which a distal end of the catheter passes when the catheter is being deployed. The first actuator mechanism is mechanically coupled to the housing and to the catheter and is controllable with a digit of a hand of the user to cause the catheter to be fed out of the catheter holder and to move along a catheter pathway of the housing toward a deployment location on the patient's body. A first port for introducing a fluid into the housing is mechanically coupled to, or integrally formed in, the housing. A first valve is mechanically coupled to the housing and is configured to be placed in at least a first position that allows fluid received in the first port to enter a first inner region of the housing and a second position that prevents fluid received in the first port from entering the first inner region of the housing. The first valve is also controllable with a digit of a hand of the user to cause the first valve to be placed in one of the first position and the second position.

Figure 2:
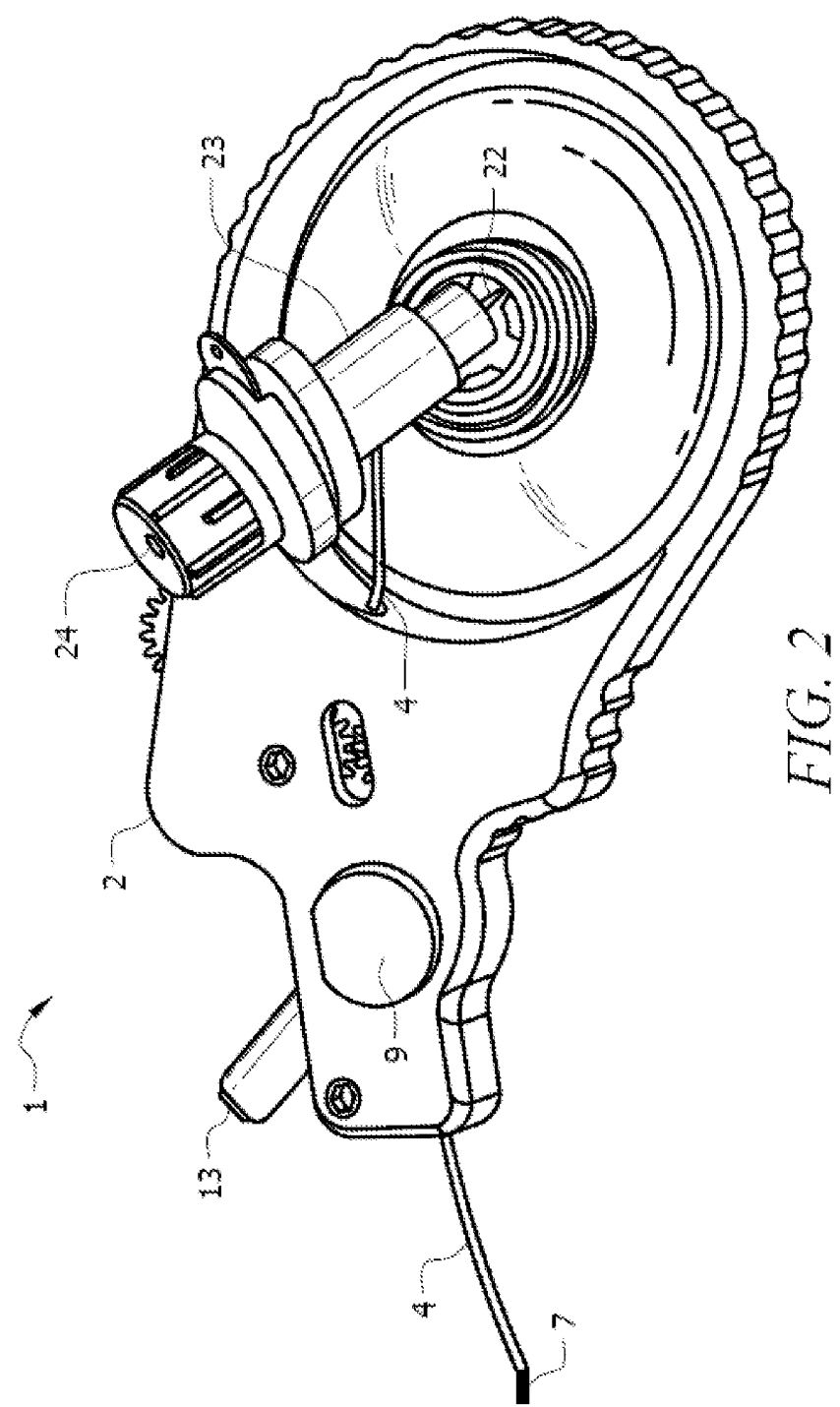
FIG. 2 is a bottom and side perspective view of the first exemplary medical device shown in FIG. 1.
Figure 3:
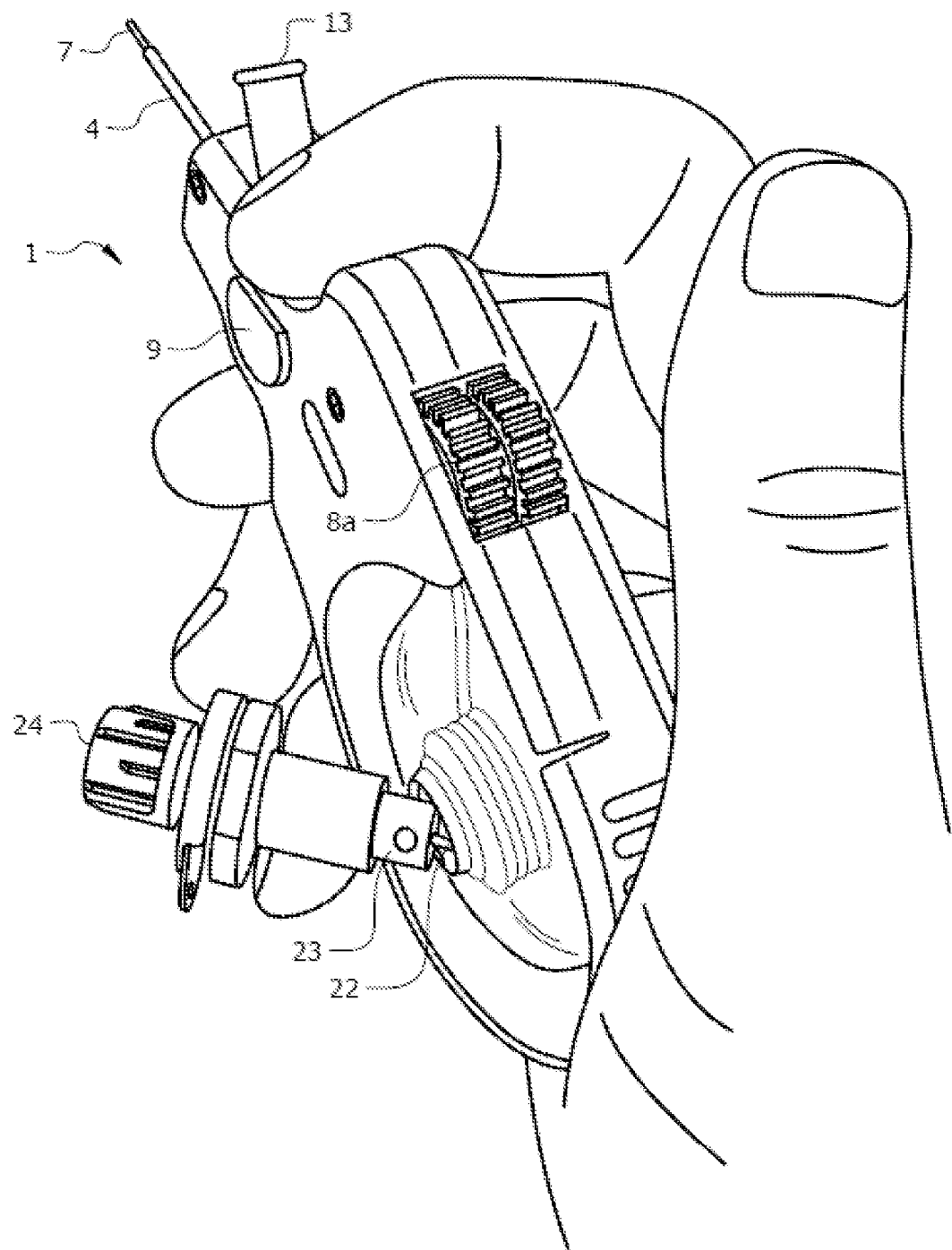
FIG. 3 is a top and side perspective view of the first exemplary medical device shown in FIG. 1.

A representative aspect of the medical device will now be described with reference to FIGS. 1-3, in which like reference numerals represent like elements, features or components. It should be noted that many variations can be made to the aspects of FIGS. 1-3 within the scope of the disclosure. The aspects shown in FIGS. 1-3 is one example of the medical device in accordance with the inventive principles and concepts that can be easily held in one hand and operated with the same hand to cause a catheter to be deployed. As will be understood by those skilled in the art in view of the description provided herein, many modifications may be made to the medical device shown in FIGS. 1-3 while still achieving the goals of the disclosure.

FIG. 1 is a side and rear transparency perspective view of a first exemplary medical device 1 according to the disclosure. FIG. 2 is a bottom and side perspective view of the medical device 1 shown in FIG. 1. FIG. 3 is a top and side perspective view of the medical device 1 shown in FIG. 1. A housing 2 of the medical device 1 has a catheter holder 3 that is configured to hold a catheter 4 (FIG. 2) in a coiled configuration. The housing 2 has a first opening 5 formed in a forward end thereof through which a distal end 7 (FIG. 2) of the catheter 4 passes when the catheter 4 is being deployed.

A first actuator mechanism 8a, 8b and 8c is mechanically coupled to the housing 2 and to the catheter 4. The first actuator mechanism 8a, 8b and 8c is controllable with a digit of a hand of the user to cause the catheter 4 to be fed out of the catheter holder 3 and to move along a catheter pathway of the housing 2 in a first direction.

A first port 13 is mechanically coupled to, or integrally formed in, the housing 2. The first port 13 is adapted to introduce a fluid into the housing 2. A first valve 9 is mechanically coupled to the housing 2 and is configured to be placed in at least a first position and a second position. In the first position, the valve 9 allows fluid received in the first port 13 to enter a first inner region 12 of the housing 2. In the second position, the first valve prevents fluid received in the first port 13 from entering the first inner region 12 of the housing 2. The first valve 9 is controllable with a digit of a hand of the user to cause the first valve 9 to be placed in one of the first position and the second position.

FIG. 3 depicts the medical device 1 being held by a user in his right hand, although it can be held and operated by either hand. The medical device 1 is controllable with the same hand in which the medical device 1 is held to cause a catheter to be placed in the patient's body. This allows the user to use the other hand to perform other tasks, such as operate an ultrasound probe. In this example, the first actuator mechanism 8a, 8b, 8c is controllable with a digit (e.g., the right thumb) of the right hand to cause the catheter 4 to be fed out of the catheter holder 3 and to move along the catheter pathway of the housing 2 in the first direction as the user operates the ultrasound probe with the left hand. The catheter pathway of the medical device 1 extends between the first opening 5 and the catheter holder 3.

As depicted in the first exemplary medical device 1, the catheter holder 3 is a disk that has a spool around which the catheter 4 is wound to give it a coiled configuration. The housing 2 can have a disk-mounting surface 15 for mounting the disk that holds the catheter 4. A spindle 16 can be fixedly secured to the disk-mounting surface 15 and extends away from the disk-mounting surface 15 in a direction substantially normal to the disk-mounting surface 15. The spindle 16 mates with an opening 18 formed in the disk to rotationally and removably couple the disk to the housing 2. The disk is removably coupled to the spindle 16 to allow it to be removed and replaced.

When the first valve 9 is in the first position, it creates a seal along the catheter pathway that seals off a second inner region 19 of the housing 2 from the first inner region 12 of the housing 2. This allows fluid that is provided to the first port 13 to enter into the first inner region 12, but prevents it from entering the second inner region 19, which is in between the first inner region 12 and the catheter holder 3. When the first valve 9 is in the second position, the catheter pathway between the second inner region 19 of the housing 2 and the first inner region 12 of the housing 2 is unblocked to allow the catheter to be deployed.

As depicted in the first exemplary medical device 1, the first valve 9 has a cylindrical body with first and second bores formed therein. The cylindrical body is movable via a digit of the user's hand in an axial direction of the cylindrical body from the first position to the second position, and vice versa. When the first valve 9 is in the first position, the first bore provides a pathway for fluid to flow from the first port 13 into the first inner region 12 of the housing 2 and to the first opening 5 formed in the forward end of the housing 2. When the first valve 9 is in the second position, the second bore provides a pathway that coincides with the catheter pathway to allow the catheter 4 to be deployed.

As the user operates the first actuator mechanism 8a, 8b, 8c with a digit (e.g., the right thumb) to deploy the catheter 4, the disk rotates to feed out the catheter 4. As depicted in the first exemplary medical device 1, the first actuator mechanism 8a, 8b and 8c has first, second and third gear wheels 8a, 8b and 8c, respectively. A portion of the first gear wheel 8a is accessible by the user to allow the user to use a digit (e.g., a thumb) to rotate the first gear wheel 8a in a second direction to cause the catheter 4 to be fed out and to move along the catheter pathway in the first direction. The user can use the other hand to operate an ultrasound probe or to perform other tasks.

The second gear wheel 8b has teeth that are engaged with teeth of the first gear wheel 8a and has teeth that are engaged with the outer surface of the catheter 4. Rotation of the first gear wheel 8a in the second direction causes the second gear wheel 8b to rotate in a third direction. The third gear wheel 8c has teeth that are engaged with the outer surface of the catheter 4. The second and third gear wheels 8b and 8c, respectively, are on opposite sides of the catheter 4. As the second gear wheel 8b rotates in the third direction, the third gear wheel 8c rotates in a fourth direction. The engagement of the teeth of the second and third gear wheels 8b and 8c, respectively, with the outer surface of the catheter and the rotation of the second and third gear wheels 8b and 8c, respectively, in the third and fourth directions, respectively, cause the catheter 4 to move along the catheter pathway in the first direction. Rotation of the first gear wheel 8a in the opposite direction causes the catheter 4 to be retracted.

As depicted in the first exemplary medical device 1, a proximal end 22 (FIG. 2) of the catheter 4 extends away from the disk-mounting surface 15 to enable the user to easily access the proximal end 22 of the catheter 4 to interconnect it with an electrical power supply. This allows an electrical current to be applied to the catheter 4 for electrically stimulating nerves. An enclosure 23 (FIG. 2) made of an electrically-insulating material is mechanically coupled to a portion of the catheter 4 that includes the proximal end 22 to enclose the proximal portion inside of the enclosure 23. The enclosure 23 may include a removable top 24 (FIG. 2) that can be removed to access the proximal end 22 of the catheter.

The medical device 1 will allow a single user to insert a needle using one hand on the medical device 1 and the user's other hand on an ultrasound probe to guide the needle to the target nerve. Once the needle is at the target nerve, the user will be able to aspirate and inject a solution through the medical device 1, if desired, with the cylindrical valve 9 in the first position to dilate the space surrounding the nerve. The cylindrical valve 9 can then be switched into the second position that allows the catheter 4 to be inserted in close proximity to the target nerve. After deploying the catheter 4, the user will be able to apply counter-traction to keep the catheter 4 in place, while the needle is being removed in a push-pull fashion, i.e., pushing, or threading, the catheter 4 while pulling the needle to withdraw it from the patient's body. If the catheter 4 contains a stylette, then this will be removed from the catheter 4. All of this will occur with a single user while the catheter 4 is maintained in a sterile and easily controlled fashion and while being able to visualize the needle and catheter 4 deployment in real time with ultrasound, if desired.

It should be noted that the invention has been described with respect to illustrative aspects for the purpose of describing the principles and concepts of the invention. The invention is not limited to these aspects. For example, while the invention has been described with reference to a particular configuration of the housing 2, the housing 2 may have any suitable configuration. Likewise, the valve 9 and the first actuator mechanism 8a, 8b and 8c may have any suitable configurations. As will be understood by those skilled in the art in view of the description being provided herein, many modifications may be made to the aspects described herein while still achieving the goals of the disclosure, and all such modifications are within the scope of the disclosure.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The present disclosure will be better understood upon viewing the following aspects which should not be confused with the claims.

Aspect 1. A medical device comprising: a housing, the housing having a catheter holder that is configured to hold a catheter in a coiled configuration, the housing having a first opening formed in a forward end thereof through which a distal end of the catheter passes when the catheter is being deployed; a first actuator mechanism mechanically coupled to the housing and to the catheter, the first actuator mechanism being controllable with a digit of a hand of the user to cause the catheter to be fed out of the catheter holder and to move along a catheter pathway of the housing in a first direction; a first port mechanically coupled to, or integrally formed in, the housing, the first port being adapted to introduce a fluid into the housing; and a first valve mechanically coupled to the housing, the first valve being configured to be placed in at least a first position that allows fluid received in the first port to enter a first inner region of the housing and a second position that prevents fluid received in the first port from entering the first inner region of the housing, the first valve being controllable with a digit of a hand of the user to cause the first valve to be placed in one of the first position and the second position.

Aspect 2. The medical device according to any one of Aspects 1-22, wherein the medical device is controllable with a first hand of a user in which the medical device is held to deploy a catheter in the patient's body while operating an ultrasound probe with a second hand of the user, wherein the first actuator mechanism is controllable with a digit of the first hand to cause the catheter to be fed out of the catheter holder and to move along the catheter pathway of the housing in a first direction as the user operates the ultrasound probe with the second hand.

Aspect 3. The medical device of any one of Aspects 1-22, wherein the first valve is controllable with a digit of the first hand of the user to cause the first valve to be placed in one of the first position and the second position as the user operates the ultrasound probe with the second hand.

Aspect 4. The medical device of any one of Aspects 1-22, wherein the catheter moves that extends between the first opening and the catheter holder the catheter pathway extends between the first opening and the catheter holder.

Aspect 5. The medical device of any one of Aspects 1-22, wherein the housing comprises a disk-mounting surface and a spindle fixedly secured to the disk-mounting surface and extending away from the disk-mounting surface in a direction substantially normal to the disk-mounting surface, the disk-mounting surface being adapted for mounting a disk thereon such that the spindle mates with an opening formed in the disk to rotationally couple the disk to the housing, wherein the coiled configuration of the catheter is stored in the disk.

Aspect 6. The medical device of any one of Aspects 1-22, wherein when the first valve is in the first position, the first valve creates a seal along the catheter pathway that seals off a second inner region of the housing from the first inner region of the housing, the second inner region being in between the first inner region and the catheter holder.

Aspect 7. The medical device of any one of Aspects 1-22, wherein when the first valve is in the second position, the catheter pathway between the second inner region of the housing and the first inner region of the housing is unblocked.

Aspect 8. The medical device of any one of Aspects 1-22, wherein the first valve comprises a cylindrical body having first and second bores formed therein, the cylindrical body being movable via a digit of the first hand of the user in an axial direction of the cylindrical body from the first position to the second position and vice versa, wherein when the first valve is in the first position, the first bore provides a pathway for fluid to flow from the first port into the first inner region of the housing and to the first opening formed in the forward end of the housing, and wherein when the first valve is in the second position, the second bore provides a pathway that coincides with the catheter pathway to allow the catheter to move along the catheter pathway between the first opening formed in the forward end of the housing and the catheter holder.

Aspect 9. The medical device of any one of Aspects 1-22, wherein the first actuator mechanism comprises: a plurality of gear wheels a portion of at least a first gear wheel of the plurality of gear wheels being accessible by the user to allow the user to use a digit of the first hand to rotate the first gear wheel in at least a second direction to cause the catheter to be fed out and to move along the catheter pathway in the first direction as the user operates the ultrasound probe with the second hand.

Aspect 10. The medical device of any one of Aspects 1-22, wherein the plurality of gear wheels includes at least a second gear wheel having teeth that are engaged with teeth of the first gear wheel and having teeth that are engaged with an outer surface of the catheter, wherein rotation of the first gear wheel in the second direction causes the second gear wheel to rotate in a third direction, and wherein rotation of the second gear wheel in the third direction causes the catheter to be fed out and to move along the catheter pathway in the first direction.

Aspect 11. The medical device of any one of Aspects 1-22, wherein the plurality of gear wheels includes at least a third gear wheel having teeth that are engaged with the outer surface of the catheter, the second and third gear wheels being on opposite sides of the catheter, wherein as the second gear wheel rotates in the third direction, the third gear wheel rotates in a fourth direction, wherein the engagement of the teeth of the second and third gear wheels with the outer surface of the catheter and the rotation of the second and third gear wheels in the third and fourth directions, respectively, cause the catheter to move along the catheter pathway in the first direction.

Aspect 12. The medical device of any one of Aspects 1-22, wherein the first actuator is controllable with a digit of the first hand to cause the catheter to be retracted and to move along the catheter pathway in a third direction as the user operates the ultrasound probe with the second hand, the third direction being substantially opposite the first direction, wherein the user causes the catheter to be retracted by using a digit of the first hand to rotate the first gear wheel in a fourth direction opposite the second direction as the user operates the ultrasound probe with the second hand.

Aspect 13. The medical device of any one of Aspects 1-22, wherein the housing comprises molded plastic.

Aspect 14. The medical device of any one of Aspects 1-22, wherein the catheter holder is configured to allow the disk to be removably rotationally coupled to the housing via the mating of the opening formed in the disk with the spindle.

Aspect 15. The medical device of any one of Aspects 1-22, wherein a proximal end of the catheter extends away from the disk-mounting surface to enable the user to easily access the proximal end of the catheter for interconnecting the proximal end of the catheter with an electrical power supply to apply an electrical current to the catheter for electrically stimulating a nerve of the patient.

Aspect 16. The medical device of any one of Aspects 1-22, further comprising: an enclosure comprising an electrically-insulating material mechanically coupled to a proximal portion of the catheter that includes the proximal end to enclose the proximal portion inside of the enclosure, the enclosure including a removable top that can be removed to access the proximal end of the catheter.

Aspect 17. A medical device that is controllable with a first hand of a user in which the medical device is held to deploy a catheter in a patient's body while operating an ultrasound probe with a second hand of the user, the medical device comprising: a housing, the housing having a disk-mounting surface and a spindle fixedly secured to the disk-mounting surface and extending away from the disk-mounting surface in a direction substantially normal to the disk-mounting surface, the disk-mounting surface being adapted for mounting a disk thereon such that the spindle mates with an opening formed in the disk to rotationally couple the disk to the housing, wherein the disk holds a coiled configuration of the catheter, the housing having a first opening formed in a forward end thereof through which a distal end of the catheter passes when the catheter is being deployed, the housing having a catheter pathway along which the catheter moves that extends between the first opening and the catheter holder; a first actuator mechanism mechanically coupled to the housing and to the catheter, the first actuator mechanism comprising a plurality of gear wheels, a portion of at least a first gear wheel of the plurality of gear wheels being accessible by the user to allow the user to use a digit of the first hand to rotate the first gear wheel in at least a first direction, wherein rotation of the first gear wheel in the first direction causes the catheter to be fed out of the disk and to move along the catheter pathway in a second direction as the user operates the ultrasound probe with the second hand; a first port mechanically coupled to, or integrally formed in, the housing, the first port being adapted to introduce a fluid into the housing; and a first valve mechanically coupled to the housing, the first valve being configured to be placed in at least a first position that allows fluid received in the first port to enter a first inner region of the housing and a second position that prevents fluid received in the first port from entering the first inner region of the housing, the first valve being controllable with a digit of the first hand to cause the first valve to be placed in one of the first position and the second position as the user operates the ultrasound probe with the second hand.

Aspect 18. The medical device of any one of Aspects 1-22, wherein when the first valve is in the first position, the first valve creates a seal along the catheter pathway that seals off a second inner region of the housing from the first inner region of the housing, the second inner region being in between the first inner region and the disk-mounting surface.

Aspect 19. The medical device of any one of Aspects 1-22, wherein when the first valve is in the second position, the catheter pathway between a second inner region of the housing and the first inner region of the housing is unblocked.

Aspect 20. The medical device of any one of Aspects 1-22, wherein the first valve comprises a cylindrical body having first and second bores formed therein, the cylindrical body being movable via a digit of the first hand of the user in an axial direction of the cylindrical body from the first position to the second position and vice versa, wherein when the first valve is in the first position, the first bore provides a pathway for fluid to flow from the first port into the first inner region of the housing and to the first opening formed in the forward end of the housing, and wherein when the first valve is in the second position, the second bore provides a pathway that coincides with the catheter pathway to allow the catheter to move along the catheter pathway between the first opening formed in the forward end of the housing and the disk.

Aspect 21. The medical device of any one of Aspects 1-22, wherein the plurality of gear wheels includes at least a second gear wheel having teeth that are engaged with teeth of the first gear wheel and having teeth that are engaged with an outer surface of the catheter, wherein rotation of the first gear wheel in the second direction causes the second gear wheel to rotate in a third direction, and wherein rotation of the second gear wheel to rotate in the third direction causes the catheter to be fed out and to move along the catheter pathway in the first direction.

Aspect 22. The medical device of any one of Aspects 1-21, wherein the plurality of gear wheels includes at least a third gear wheel having teeth that are engaged with the outer surface of the catheter, the second and third gear wheels being on opposite sides of the catheter, wherein as the second gear wheel rotates in the third direction, the third gear wheel rotates in a fourth direction, wherein the engagement of the teeth of the second and third gear wheels with the outer surface of the catheter and the rotation of the second and third gear wheels in the third and fourth directions, respectively, cause the catheter to move along the catheter pathway in the first direction.

Aspect 23. A method for use by a user to deploy a catheter in a patient's body, the method comprising: with a digit of a hand of the user, controlling a first actuator mechanism that is mechanically coupled to a housing of the medical device and to the catheter to cause the catheter to be fed out of a coiled configuration of the catheter held within a catheter holder and to move along a catheter pathway in a first direction, the housing having a first opening formed in a forward end thereof through which a distal end of the catheter passes when the catheter is being deployed; and with a digit of a hand of the user, operating a first valve that is mechanically coupled to the housing to place the first valve in one of a first position and a second position, wherein when the first valve is in the first position, the first valve allows fluid received in a first port of the medical device to enter a first inner region of the housing, wherein when the first valve is the second position, the first valve prevents fluid received in the first port from entering the first inner region of the housing.

Aspect 24. The method of Aspect 23 performed with a device according to any one of Aspects 1-22.

We claim:

1. A medical device comprising:
   a housing, the housing having a catheter holder that is configured to hold a catheter in a coiled configuration, the housing having a first opening formed in a forward end thereof through which a distal end of the catheter passes when the catheter is being deployed;
   a first actuator mechanism mechanically coupled to the housing and to the catheter, the first actuator mechanism being controllable with a digit of a hand of a user to cause the catheter to be fed out of the catheter holder and to move along a catheter pathway of the housing in a first direction;
   a first port mechanically coupled to, or integrally formed in, the housing, the first port being adapted to introduce a fluid into the housing; and
   a first valve mechanically coupled to the housing, the first valve being configured to be placed in at least a first position that allows fluid received in the first port to enter a first inner region of the housing and a second position that prevents fluid received in the first port from entering the first inner region of the housing, the first valve being controllable with a digit of a hand of the user to cause the first valve to be placed in one of the first position and the second position,
   wherein the first valve comprises a cylindrical body having first and second bores formed therein, the cylindrical body being movable via a digit of the first hand of the user in an axial direction of the cylindrical body from the first position to the second position and vice versa, wherein when the first valve is in the first position, the first bore provides a pathway for fluid to flow from the first port into the first inner region of the housing and to the first opening formed in the forward end of the housing, and wherein when the first valve is in the second position, the second bore provides a pathway that coincides with the catheter pathway to allow the catheter to move along the catheter pathway between the first opening formed in the forward end of the housing and the catheter holder.

2. The medical device of claim 1, wherein the medical device is controllable with a first hand of a user in which the medical device is held to deploy a catheter in a patient's body while operating an ultrasound probe with a second hand of the user, wherein the first actuator mechanism is controllable with a digit of the first hand to cause the catheter to be fed out of the catheter holder and to move along the catheter pathway of the housing in a first direction as the user operates the ultrasound probe with the second hand.

3. The medical device of claim 2, wherein the first valve is controllable with a digit of the first hand of the user to cause the first valve to be placed in one of the first position and the second position as the user operates the ultrasound probe with the second hand.

4. The medical device of claim 3, wherein the catheter pathway extends between the first opening and the catheter holder.

5. The medical device of claim 1, wherein the housing comprises a disk-mounting surface and a spindle fixedly secured to the disk-mounting surface and extending away from the disk-mounting surface in a direction normal to the disk-mounting surface, the disk-mounting surface being adapted for mounting a disk thereon such that the spindle mates with an opening formed in the disk to rotationally couple the disk to the housing, wherein the coiled configuration of the catheter is stored in the disk.

6. The medical device of claim 5, wherein when the first valve is in the first position, the first valve creates a seal along the catheter pathway that seals off a second inner region of the housing from the first inner region of the housing, the second inner region being in between the first inner region and the catheter holder, and wherein when the first valve is in the second position, the catheter pathway between the second inner region of the housing and the first inner region of the housing is unblocked.

7. The medical device of claim 5, wherein the first actuator mechanism comprises:
 a plurality of gear wheels a portion of at least a first gear wheel of the plurality of gear wheels being accessible by the user to allow the user to use a digit of the first hand to rotate the first gear wheel in at least a second direction to cause the catheter to be fed out and to move along the catheter pathway in the first direction as the user operates an ultrasound probe with the second hand.

8. The medical device of claim 7, wherein the plurality of gear wheels includes at least a second gear wheel having teeth that are engaged with teeth of the first gear wheel and having teeth that are engaged with an outer surface of the catheter, wherein rotation of the first gear wheel in the second direction causes the second gear wheel to rotate in a third direction, and wherein rotation of the second gear wheel in the third direction causes the catheter to be fed out and to move along the catheter pathway in the first direction.

9. The medical device of claim 8, wherein the plurality of gear wheels includes at least a third gear wheel having teeth that are engaged with the outer surface of the catheter, the second and third gear wheels being on opposite sides of the catheter, wherein as the second gear wheel rotates in the third direction, the third gear wheel rotates in a fourth direction, wherein the engagement of the teeth of the second and third gear wheels with the outer surface of the catheter and the rotation of the second and third gear wheels in the third and fourth directions, respectively, cause the catheter to move along the catheter pathway in the first direction.

10. The medical device of claim 7, wherein the first actuator is controllable with a digit of the first hand to cause the catheter to be retracted and to move along the catheter pathway in a third direction as the user operates the ultrasound probe with the second hand, the third direction being opposite the first direction, wherein the user causes the catheter to be retracted by using a digit of the first hand to rotate the first gear wheel in a fourth direction opposite the second direction as the user operates the ultrasound probe with the second hand.

11. The medical device of claim 7, wherein the catheter holder is configured to allow the disk to be removably rotationally coupled to the housing via the mating of the opening formed in the disk with the spindle.

12. The medical device of claim 5, wherein a proximal end of the catheter extends away from the disk-mounting surface to enable the user to easily access the proximal end of the catheter for interconnecting the proximal end of the catheter with an electrical power supply to apply an electrical current to the catheter for electrically stimulating a nerve of a patient.

13. The medical device of claim 12, further comprising:
 an enclosure comprising an electrically-insulating material mechanically coupled to a proximal portion of the catheter that includes the proximal end to enclose the proximal portion inside of the enclosure, the enclosure including a removable top that can be removed to access the proximal end of the catheter.

14. A medical device that is controllable with a first hand of a user in which the medical device is held to deploy a catheter in a patient's body while operating an ultrasound probe with a second hand of the user, the medical device comprising:
 a housing, the housing having a disk-mounting surface and a spindle fixedly secured to the disk-mounting surface and extending away from the disk-mounting surface in a direction normal to the disk-mounting surface, the disk-mounting surface being adapted for mounting a disk thereon such that the spindle mates with an opening formed in the disk to rotationally couple the disk to the housing, wherein the disk holds a coiled configuration of the catheter, the housing having a first opening formed in a forward end thereof through which a distal end of the catheter passes when the catheter is being deployed, the housing having a catheter pathway along which the catheter moves that extends between the first opening and the disk;
 a first actuator mechanism mechanically coupled to the housing and to the catheter, the first actuator mechanism comprising a plurality of gear wheels, a portion of at least a first gear wheel of the plurality of gear wheels being accessible by the user to allow the user to use a digit of the first hand to rotate the first gear wheel in at least a first direction, wherein rotation of the first gear wheel in the first direction causes the catheter to be fed out of the disk and to move along the catheter pathway in a second direction as the user operates the ultrasound probe with the second hand;
 a first port mechanically coupled to, or integrally formed in, the housing, the first port being adapted to introduce a fluid into the housing; and
 a first valve mechanically coupled to the housing, the first valve being configured to be placed in at least a first position that allows fluid received in the first port to enter a first inner region of the housing and a second position that prevents fluid received in the first port from entering the first inner region of the housing, the first valve being controllable with a digit of the first hand to cause the first valve to be placed in one of the first position and the second position as the user operates the ultrasound probe with the second hand,
 wherein the first valve comprises a cylindrical body having first and second bores formed therein, the cylindrical body being movable via a digit of the first hand of the user in an axial direction of the cylindrical body from the first position to the second position and vice versa, wherein when the first valve is in the first position, the first bore provides a pathway for fluid to flow from the first port into the first inner region of the housing and to the first opening formed in the forward end of the housing, and wherein when the first valve is in the second position, the second bore provides a pathway that coincides with the catheter pathway to allow the catheter to move along the catheter pathway between the first opening formed in the forward end of the housing and the disk.

15. The medical device of claim 14, wherein when the first valve is in the first position, the first valve creates a seal along the catheter pathway that seals off a second inner region of the housing from the first inner region of the housing, the second inner region being in between the first inner region and the disk-mounting surface, wherein when the first valve is in the second position, the catheter pathway between a second inner region of the housing and the first inner region of the housing is unblocked.

16. The medical device of claim 14, wherein the plurality of gear wheels includes at least a second gear wheel having teeth that are engaged with teeth of the first gear wheel and having teeth that are engaged with an outer surface of the catheter, wherein rotation of the first gear wheel in the second direction causes the second gear wheel to rotate in a third direction, and wherein rotation of the second gear wheel to rotate in the third direction causes the catheter to be fed out and to move along the catheter pathway in the first direction.

17. The medical device of claim 16, wherein the plurality of gear wheels includes at least a third gear wheel having teeth that are engaged with the outer surface of the catheter, the second and third gear wheels being on opposite sides of the catheter, wherein as the second gear wheel rotates in the third direction, the third gear wheel rotates in a fourth direction, wherein the engagement of the teeth of the second and third gear wheels with the outer surface of the catheter and the rotation of the second and third gear wheels in the third and fourth directions, respectively, cause the catheter to move along the catheter pathway in the first direction.

18. A method for use by a user to deploy a catheter in a patient's body, the method comprising:

with a digit of a hand of a user of a medical device, controlling a first actuator mechanism that is mechanically coupled to a housing of the medical device and to the catheter to cause the catheter to be fed out of a coiled configuration of the catheter held within a catheter holder of the medical device and to move along a catheter pathway in a first direction, the housing having a first opening formed in a forward end thereof through which a distal end of the catheter passes when the catheter is being deployed; and with a digit of a hand of the user, operating a first valve that is mechanically coupled to the housing to place the first valve in one of a first position and a second position, wherein when the first valve is in the first position, the first valve allows fluid received in a first port of the medical device to enter a first inner region of the housing, wherein when the first valve is the second position, the first valve prevents fluid received in the first port from entering the first inner region of the housing, wherein the first valve comprises a cylindrical body having first and second bores formed therein, the cylindrical body being movable via a digit of the first hand of the user in an axial direction of the cylindrical body from the first position to the second position and vice versa, wherein when the first valve is in the first position, the first bore provides a pathway for fluid to flow from the first port into the first inner region of the housing and to the first opening formed in the forward end of the housing, and wherein when the first valve is in the second position, the second bore provides a pathway that coincides with the catheter pathway to allow the catheter to move along the catheter pathway between the first opening formed in the forward end of the housing and the catheter holder.

* * * * *